US007252838B2

(12) United States Patent
O'Conner et al.

(10) Patent No.: US 7,252,838 B2
(45) Date of Patent: *Aug. 7, 2007

(54) DRUG RELEASING ELASTIC BAND AND METHOD

(75) Inventors: Marcia L. O'Conner, Bolton, MA (US); Michael S. Banik, Bolton, MA (US); Kathleen M. Miller, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 561 days.

This patent is subject to a terminal disclaimer.

(21) Appl. No.: 10/244,440

(22) Filed: Sep. 17, 2002

(65) Prior Publication Data

US 2003/0012806 A1 Jan. 16, 2003

Related U.S. Application Data (63) Continuation of application No. 09/328,665, filed on Jun. 9, 1999, now Pat. No. 6,471,987.

(51) Int. Cl.
*A61B 17/12* (2006.01)
*A61L 31/14* (2006.01)
*A61L 31/16* (2006.01)

(52) U.S. Cl. ............... 424/447; 424/422; 424/423; 424/424; 424/426; 424/443; 424/444; 424/484; 424/485; 424/486; 514/772; 514/772.3; 514/782; 514/953; 606/151; 606/157

(58) Field of Classification Search ............ 424/422, 424/423, 424, 426, 443, 444, 446, 447, 448, 424/449, 484, 486, 772, 776.3, 782, 963; 606/151, 157, 140; 514/772, 772.3, 782, 514/963

See application file for complete search history.

(56) References Cited

U.S. PATENT DOCUMENTS 5,269,789 A * 12/1993 Chin et al. .................. 606/140

| 5,356,416 | A | * | 10/1994 | Chu et al. ................... 606/140 |
| 5,419,913 | A | * | 5/1995 | Podell et al. ................ 424/448 |
| 5,443,458 | A | | 8/1995 | Eury |
| 5,618,286 | A | | 4/1997 | Brinker |
| 5,697,940 | A | * | 12/1997 | Chu et al. ................... 606/140 |
| 6,471,987 | B1 | * | 10/2002 | McBride-Sakal et al. ... 424/447 |

FOREIGN PATENT DOCUMENTS

| EP | 0 477 020 | 3/1992 |
| WO | WO 89/04674 | 6/1989 |
| WO | WO 98/55028 | 10/1998 |

OTHER PUBLICATIONS

Wikipedia, the free encyclopedia (http://en.wikipedia.org/wiki/Alimentary_tract) (2006), "Gastrointestinal tract".*
PDR® Electronic Library™: Stedman Definition (2002-2006) (http://www.thomsonhc.com/pdrel/librarian/PFDefaultActionId/pdrcommon. Stedmans), Stedman's Medical Dictionary (27th Ed. 2000), "orthodontics".*
PDR® Electronic Library™: Stedman Definition (2002-2006) (http://www.thomsonhc.com/pdrel/librarian/PFDefaultActionId/pdrcommon. Stedmans), Stedman's Medical Dictionary (27th Ed. 2000), "chemotherapeutic".*
PDR® Electronic Library™: Stedman Definition (2002-2006) (http://www.thomsonhc.com/pdrel/librarian/PFDefaultActionId/pdrcommon. Stedmans), Stedman's Medical Dictionary (27th Ed. 2000), "chemotherapy".*

* cited by examiner

*Primary Examiner*—Johann Richter
*Assistant Examiner*—Frank I Choi
(74) *Attorney, Agent, or Firm*—Kenyon & Kenyon LLP (57) ABSTRACT

A ligating band according to the present invention comprises an elastomeric layer and an inner drug releasing layer. The inner drug releasing layer includes a therapeutic agent, for example a chemotherapeutic agent for treating a mucosa, polyp or other growth. A ligating band according to the present invention also may include an inner diffusion barrier disposed between the elastomeric layer and the inner drug releasing layer, with the elastomeric layer and the inner drug releasing layer each contacting the inner diffusion barrier.

20 Claims, 6 Drawing Sheets

DRUG RELEASING ELASTIC BAND AND METHOD

CROSS-REFERENCE TO RELATED APPLICATIONS

This application is a Continuation of application Ser. No. 09/328,665, filed Jun. 9, 1999, now U.S. Pat. No. 6,471,987, which is incorporated herein in its entirety by reference thereto.

FIELD OF THE INVENTION

The present invention relates to tissue ligation, and in particular a ligating band which releases a drug, for example a chemotherapeutic agent.

BACKGROUND INFORMATION

Endoscopic ligation is often used to treat polyps or other growths inside the body. For example, pre-malignant gastrointestinal mucosa are often removed using an endoscopic snare, and endoscopic ligation may be employed to remove surrounding residual or base tissue, particularly when biopsy of the earlier-removed tissue indicates a foci of cancer. In other cases, mucosa may be removed by delivering a ligating band to the base of the mucosa. The ligating band restricts blood flow to the ligated tissue, leading to eventual necrosis.

One problem with treating pre-malignant or malignant mucosa endoscopically is that the base of the malignancy may not undergo necrosis. If some malignant or pre-malignant cells are left surviving, there is a risk that the residual cancer cells will spread further. For this reason, many physicians opt for surgical treatment of such mucosa. However, surgical resection is not desirable or even possible for some patients, and surgical recision is a much more invasive and complicated procedure, even for more healthy patients.

SUMMARY OF THE INVENTION

A ligating band according to the present invention comprises an elastomeric layer and an inner drug releasing layer. The inner drug releasing layer includes a therapeutic agent, for example a chemotherapeutic agent. A ligating band according to the present invention also may include an inner diffusion barrier disposed between the elastomeric layer and the inner drug releasing layer, with the elastomeric layer and the inner drug releasing layer each contacting the inner diffusion barrier.

DETAILED DESCRIPTION

Figure 1:
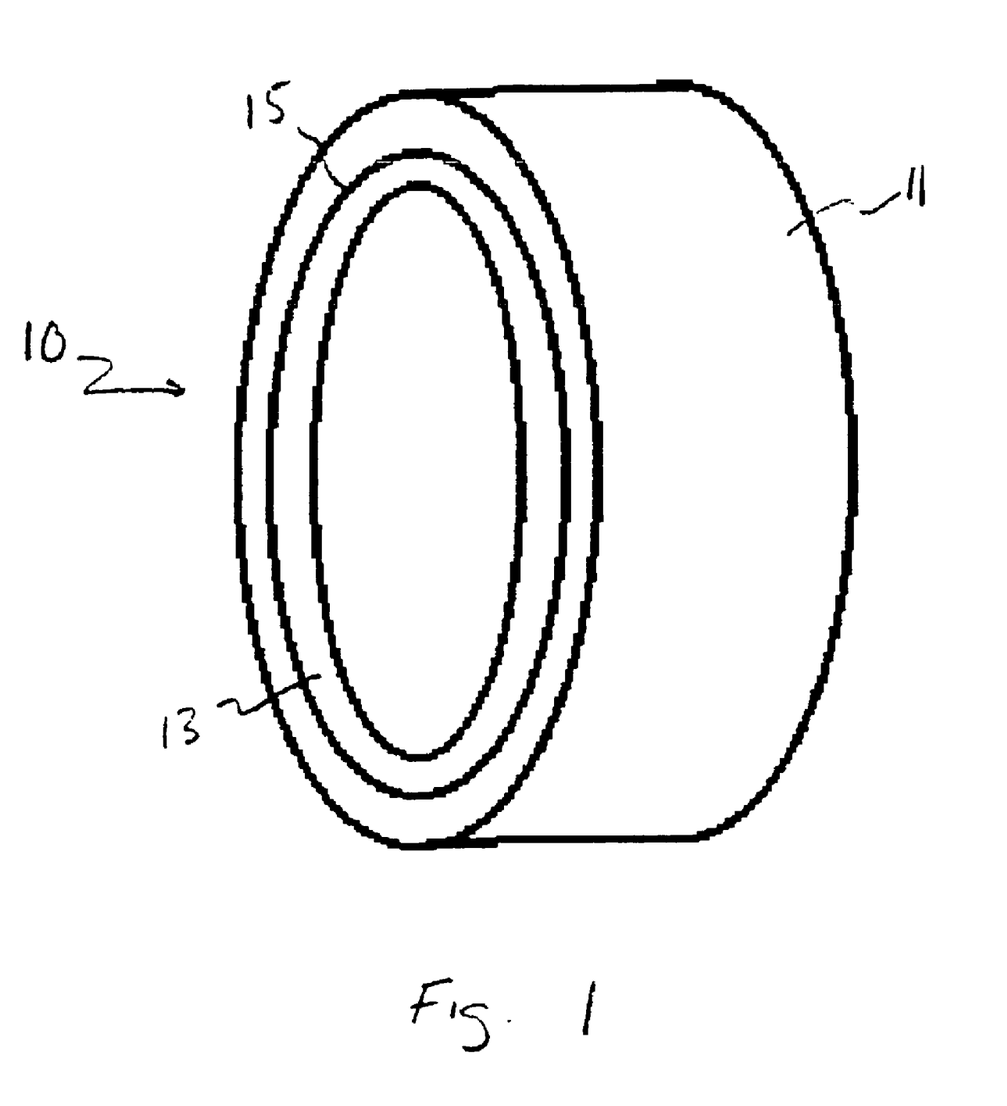
FIG. 1 is a perspective view of an exemplary embodiment of a ligating band according to the present invention.

FIG. 1 illustrates an exemplary embodiment of a ligating band 10 according to the present invention. In general, it is understood that a ligating band according to the present invention may be delivered using any suitable delivery device or mechanism, such as a ligating band dispenser. Such a device may include, for example, a tip or a cylindrical end over which one or more ligating bands may be stretched. Tissue to be ligated may be drawn into an interior recess of the tip or cylindrical end, and a band released around the base of the tissue. Such tissue may include pre-malignant or malignant mucosa, other polyps, varices, ulcers, or any other type of tissue. For convenience, any tissues to be ligated are referred to herein as mucosa, but it is understood that this term includes the above types of tissue as well as any other tissue which may be subject to ligation. Likewise, it is understood that the term "ligating band" should be generally construed herein to include any suitable elastic band, and the term "ligation" should be generally construed to include any suitable procedure for delivering such a band.

In the exemplary embodiment of FIG. 1, ligating band 10 includes an elastomeric layer 11 and an inner drug releasing layer 13. Elastomeric layer 11 and inner drug releasing layer 13 may be separated by an inner diffusion barrier 15, 50 that each contacts inner diffusion barrier 15. Elastomeric layer 11 preferably provides an elastic force to retain ligating band 10 in place around the base of a mucosa. Elastomeric layer 11 is therefore preferably a material having a relatively high elasticity. Elastomeric layer 11 may also be relatively impervious to destruction within the body, so that the elasticity of elastomeric layer 11 does not significantly decrease over time.

Inner drug releasing layer 13 may be impregnated or coated with a therapeutic agent, for example a time-released therapeutic agent, that may treat a ligated mucosa or the surrounding tissue. While any material may be used, inner drug releasing layer 13 preferably is formed from a biodegradable material, for example a biodegradable polymer, that breaks down over time. Many biodegradable materials are readily impregnated or coated with therapeutic agents, and the processing parameters for loading drugs into biodegradable materials are well established for many such materials. In addition, use of a biodegradable material for inner drug releasing layer 13 allows for lower processing temperatures during manufacture. The lower processing temperature helps prevent drug degradation and expands the arsenal of therapeutics that may be used in conjunction with a ligating band 10 according to the present invention. Preferred materials include polylactic acid (PLA or PLLA), polyglyatic acid (PGA) polycaprolactone, polyanhydride, poly (ortho ester), and similar materials.

In the case of pre-malignant or malignant mucosa, the therapeutic agent may include a chemotherapeutic agent. A chemotherapeutic agent may then assist in the destruction of the mucosa. Alternatively, it is often advantageous to remove a portion of the mucosa for study. In this case, the chemotherapeutic agent may assist in destroying any residual pre-malignant or malignant tissue at the base of the mucosa or in the surrounding area. Preferably, the chemotherapeutic agent includes 5-fluorouracil, but any suitable chemotherapeutic agent may be used. Other types of therapeutic agents may also be used in addition to or in conjunction with chemotherapeutic agents, for example anti-inflammatories, coagulants, steroids, antibiotics, monoclonal antibodies, growth factors, cellular inhibitors, genetic therapeutics, or other suitable therapeutics.

Inner diffusion barrier 15 is disposed between elastomeric layer 11 and inner drug releasing layer 13. Inner diffusion barrier 15 prevents the therapeutic of inner drug releasing layer 13 from leaching into elastomeric layer 11 and into the body. Any suitable material may be used for inner diffusion barrier 15, but preferably the material is hydrophobic. Preferred materials include ethylene vinyl acetate, polyurethane, non-woven polyester sheeting, and other synthetic or natural elastomeric materials.

Figure 2:
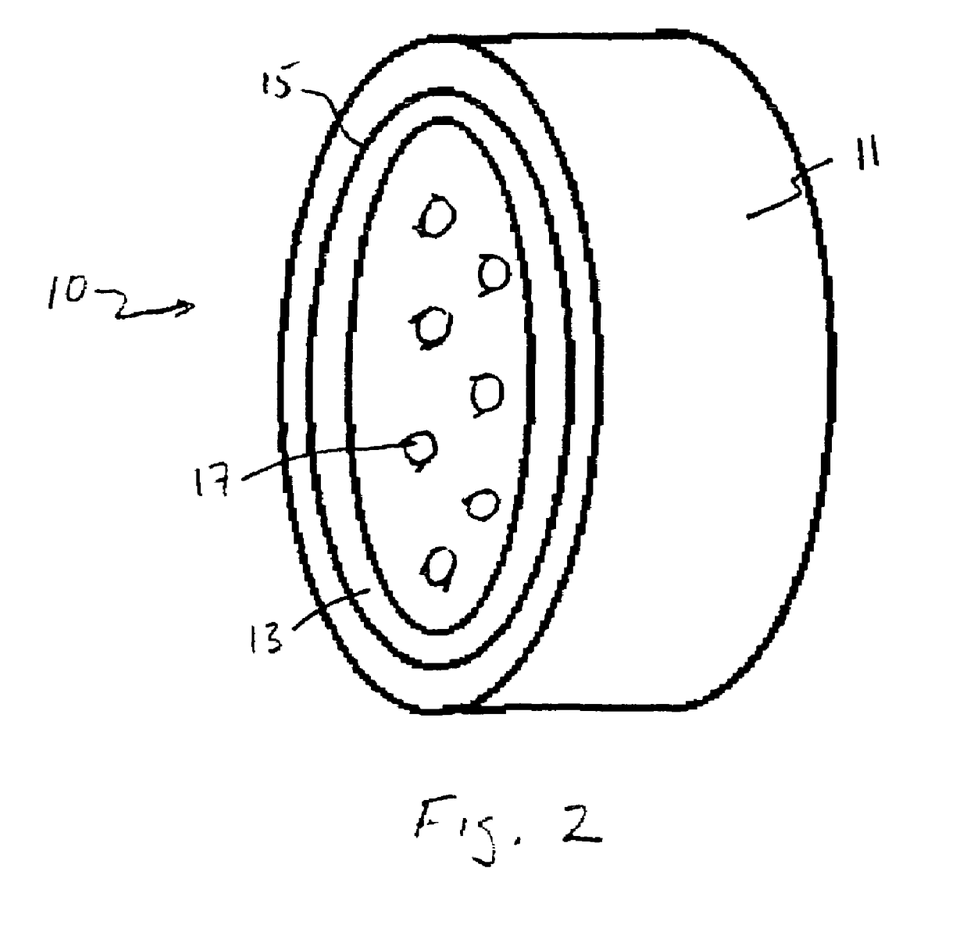
FIG. 2 is a perspective view of a second exemplary embodiment of a ligating band according to the present invention.

FIG. 2 illustrates an exemplary feature of a ligating band 10 according to the present invention. In some situations, for example when ligating mucosa in the digestive tract, ligating bands have a tendency to slip off the mucosa. This is sometimes due to natural tension created by ligation. In the digestive tract, this problem is exacerbated by peristaltic contractions. For this reason, it is advantageous in some situations to provide protrusions 17 on inner drug releasing layer 13. Protrusions 17 extend into the mucosa and help maintain ligating band 10 in place. In addition, protrusions 17 assist in delivering the therapeutic agent to the target site. Preferably protrusions 17 include any therapeutic agent present on or within inner drug releasing layer 13, and may be constructed integral with inner drug releasing layer, if desired.

Figure 3:
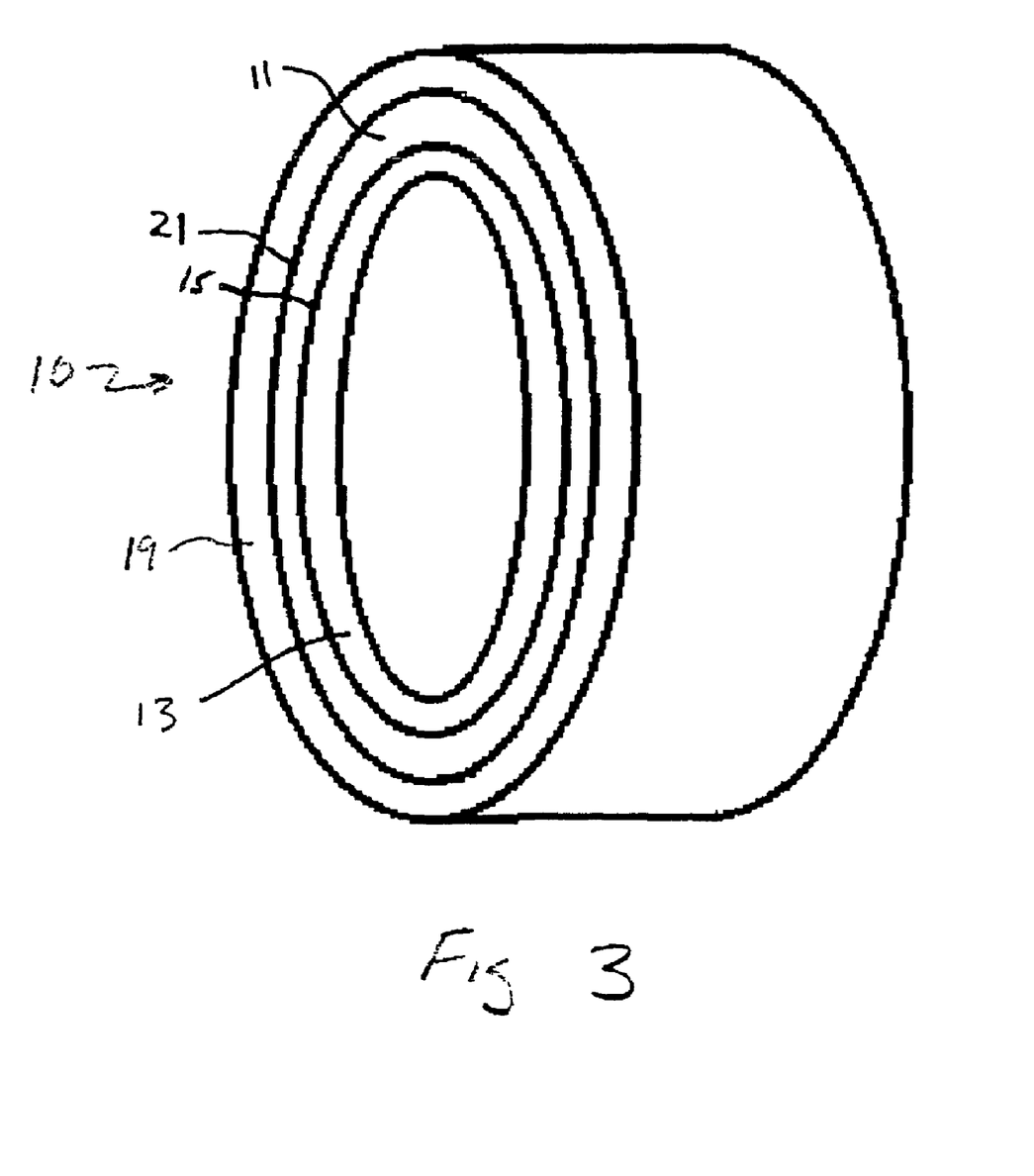
FIG. 3 is a perspective view of a third exemplary embodiment of a ligating band according to the present invention.
Figure 4:
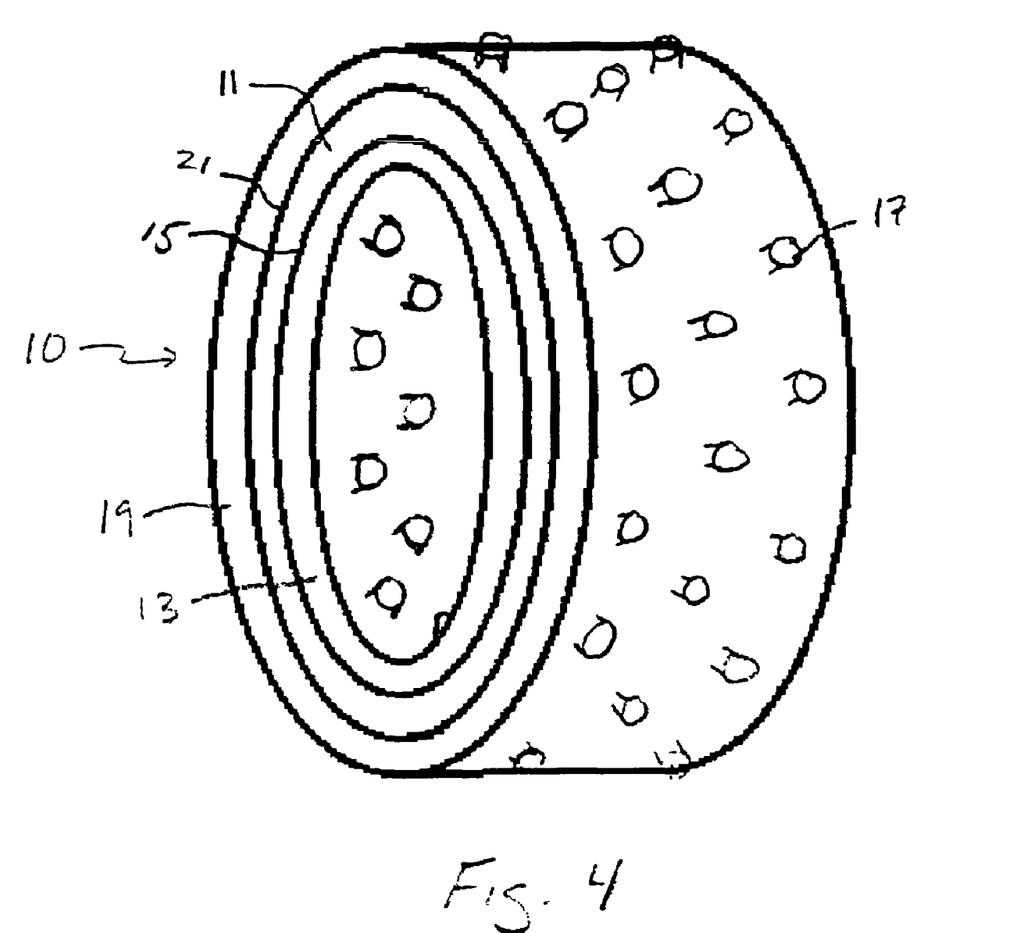
FIG. 4 is a perspective view of a fourth exemplary embodiment of a ligating band according to the present invention.

FIG. 3 shows another exemplary ligating band 10 according to the present invention. Some ligating band dispensers tend to roll the ligating band off a cylindrical end portion. Other ligating bands, even if not designed to have ligating bands roll during delivery, may allow the ligating band to become inverted during delivery. That is, the intended inner surface of the ligating band may end up facing outwardly. A ligating band 10 according to the present invention may therefore include an outer drug releasing layer 19, which may be separated from elastomeric layer 11 by an outer diffusion barrier 21. Outer drug releasing layer 19 and outer diffusion barrier 21 may be constructed from the same materials as inner drug releasing layer 13 and inner diffusion barrier 15, respectively, and outer drug releasing layer 19 preferably includes any therapeutics included on inner drug releasing layer 13. In this manner, if ligating band 10 is rotated inside-out during deployment, it may still administer the intended therapeutic or therapeutics to the target site. A ligating band 10 having outer drug releasing layer may also include protrusions 17 on either of inner and outer drug releasing layers, as illustrated in FIG. 4.

Figure 5:
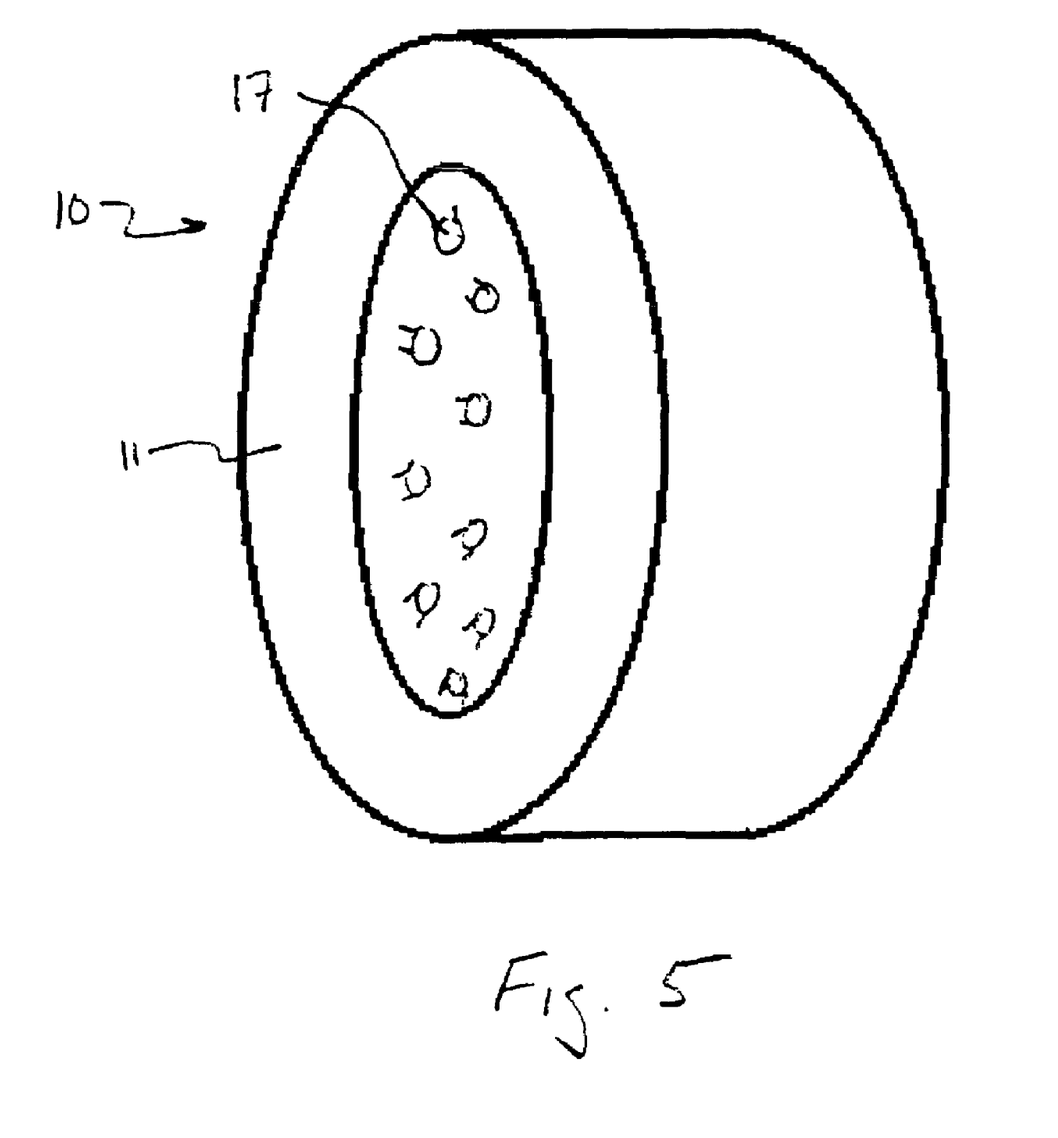
FIG. 5 is a perspective view of a fifth exemplary embodiment of a ligating band according to the present invention.

FIG. 5 illustrates an exemplary embodiment of a ligating band 10 according to the present invention, in which no inner drug releasing layer 13 or diffusion barrier 15, 21 are provided. In this embodiment, protrusions 17 are disposed directly on elastomeric layer 11. Protrusions 17 are embedded or coated with any desired therapeutic agents such as chemotherapeutic agents, and deliver the agents directly to the mucosa. Protrusions 17 are preferably formed of polycaprolactone, polyanhydride, poly (ortho ester), or a similar material, although any suitable material may be used.

Figures 6, 7:
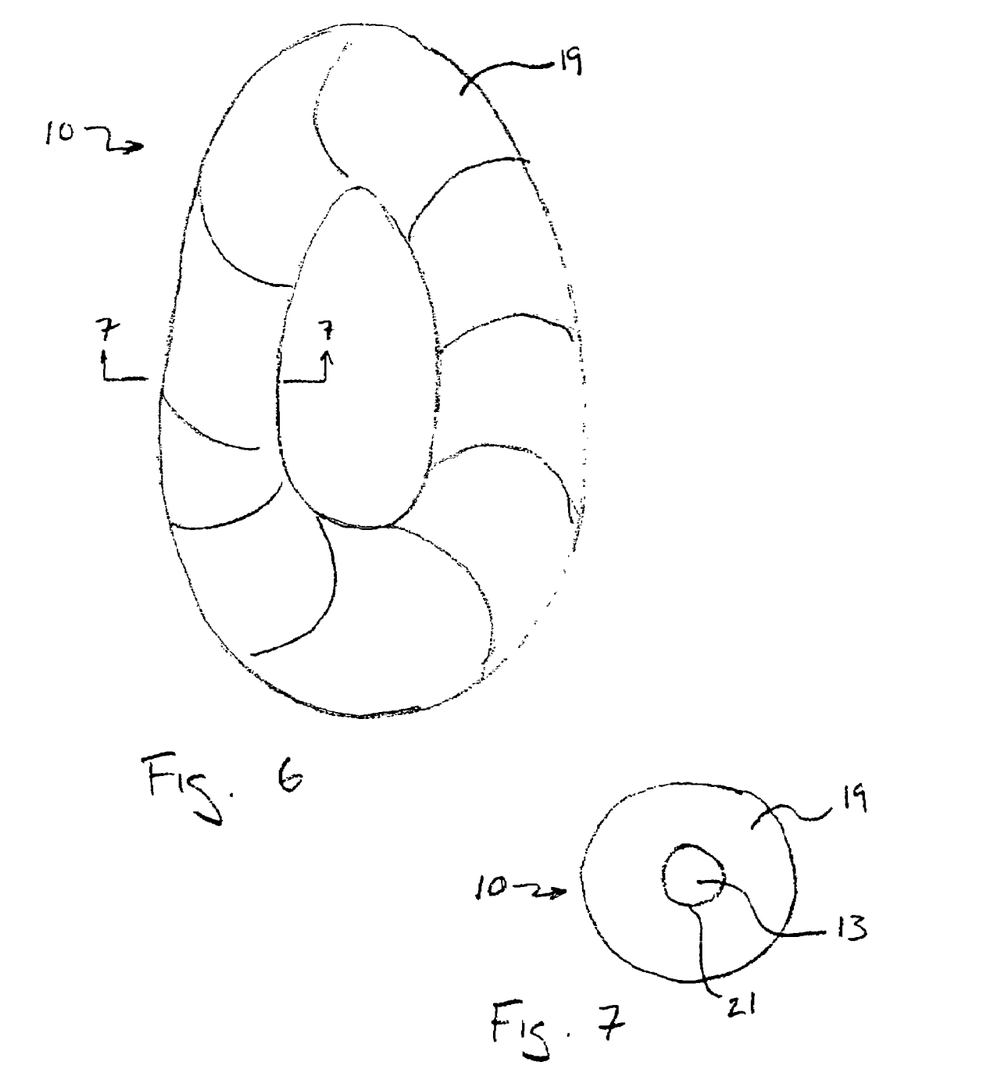
FIG. 6 is a perspective view of a sixth exemplary embodiment of a ligating band according to the present invention.
FIG. 7 is a cross-sectional view of the ligating band of FIG. 6, taken along the line 7-7 of FIG. 6.

FIGS. 6 and 7 illustrate an exemplary embodiment of a ligating band 10 according to the present invention also designed for delivery mechanisms that tend to roll the band. In this embodiment, ligating band 10 has a circular cross-section, as illustrated in FIG. 7. Specifically, elastomeric layer 13 is provided as an inner core, and is surrounded by outer drug releasing layer 19. As in other embodiments, the two layers 13, 19 are preferably separated by an outer diffusion barrier 21 (the term "outer" being used merely for convenience, as it was used for convenience in the description above). A ligating band 10 according to FIGS. 6 and 7 may also include protrusions 17 (not shown in FIGS. 6 and 7). The circular cross-section of a ligating band according to this embodiment ensures that outer drug releasing layer 19 will be in contact with the ligated mucosa, regardless of any rolling during deployment.

In an exemplary method of ligating tissue according to the present invention, a portion of tissue may first be removed, if desired, by any endoscopic procedure. This prior removal may be performed in order to retrieve tissue for biopsy, for example, or for any other suitable reason. Regardless of whether any "prior" tissue is removed, a ligating band dispenser may be introduced and delivered to the intended site. Tissue is then drawn into a recess of the ligating band dispenser, and a ligating band 10 including a chemotherapeutic or other therapeutic agent is delivered around the base of the tissue.

A ligating band and method according to the present invention has been described with respect to several exemplary embodiments. It can be understood, however, that there are many other variations of the above described embodiments which will be apparent to those skilled in the art. It is understood that these modifications are within the teaching of the present invention, which is to be limited only by the claims appended hereto.

What is claimed is:

1. A ligating band comprising:
   an elastomeric layer;
   an inner drug releasing layer, the inner drug releasing layer including a therapeutic agent; and
   an inner diffusion barrier disposed between the elastomeric layer and the inner drug releasing layer, each of the elastomeric layer and the inner drug releasing layer contacting the inner diffusion barrier; wherein the ligating band forms a continuous elastic perimeter about an open center area for ligating tissue.

2. The ligating band according to claim 1, wherein the therapeutic agent includes a chemotherapeutic agent.

3. The ligating band according to claim 1, wherein the inner drug releasing layer is biodegradable.

4. The ligating band according to claim 1, further comprising at least one protrusion disposed on the inner drug releasing layer, the at least one protrusion including the therapeutic agent.

5. The ligating band according to claim 4, wherein the at least one protrusion is integral with the inner drug releasing layer.

6. The ligating band according to claim 4, wherein the therapeutic agent includes a chemotherapeutic agent.

7. The ligating band according to claim 1, further comprising:
   an outer drug releasing layer, the outer drug releasing layer including the therapeutic agent; and
   an outer diffusion barrier disposed between the elastomeric layer and the outer drug releasing layer, each of the elastomeric layer and the outer drug releasing layer contacting the outer diffusion barrier.

8. The ligating band according to claim 7 wherein the therapeutic agent includes a chemotherapeutic agent.

9. The ligating band according to claim 7, wherein the inner and outer drug releasing layers are biodegradable.

10. The ligating band according to claim 7, further comprising at least one inner protrusion disposed on the inner drug releasing layer and at least one outer protrusion disposed on the outer drug releasing layer, the at least one inner protrusion and the at least one outer protrusion including the therapeutic agent.

11. The ligating band according to claim 1, wherein the ligating band is circular in cross-section, the elastomeric layer being surrounded by the inner drug releasing layer.

12. The ligating band according to claim 11, wherein the therapeutic agent includes a chemotherapeutic agent.

13. The ligating band according to claim 11, wherein the inner drug releasing layer is biodegradable.

14. The ligating band according to claim 11, further comprising at least one protrusion disposed on the inner drug releasing layer, the at least one protrusion including the therapeutic agent.

15. A method of ligating tissue using a ligating band dispenser, the ligating band dispenser including a tip having a recess, comprising:
    drawing the tissue into the recess of the tip of the ligating band dispenser; and
    deploying a ligating band around a base of the tissue, wherein the ligating band forms a continuous elastic perimeter about an open center area for ligating tissue and includes an inner drug releasing layer in contact with an elastomeric layer, the inner drug releasing layer including a therapeutic agent, and an inner diffusion barrier disposed between the elastomeric layer and the inner drug releasing layer, each of the elastomeric layer and the inner drug releasing layer contacting the inner diffusion barrier.

16. The method according to claim 15, further comprising, prior to drawing the tissue, removing a portion of the tissue.

17. The method according to claim 15, further comprising, after deploying the ligating band, removing a portion of the tissue.

18. The method of claim 15, wherein the therapeutic agent is a chemotherapeutic agent.

19. The method of claim 15, wherein the ligating band further comprises at least one protrusion, the at least one protrusion including the therapeutic agent.

20. The ligating band according to claim 15, wherein the inner drug releasing layer is biodegradable.

* * * * *

UNITED STATES PATENT AND TRADEMARK OFFICE
CERTIFICATE OF CORRECTION

PATENT NO. : 7,252,838 B2  Page 1 of 1
APPLICATION NO. : 10/244440
DATED : August 7, 2007
INVENTOR(S) : O'Conner et al.

It is certified that error appears in the above-identified patent and that said Letters Patent is hereby corrected as shown below:

Column 2, line 29, "barrier 15, 50 that" should be changed to --barrier 15, so that--;

Column 2, line 55, "polyglyatic acid (PGA)" should be changed to --polyglycolic acid (PGA)--;

Column 3, line 16, "when ligating mucosa in the digestive tract" should be changed to --when a ligating mucosa is in the digestive tract--; and Column 3, line 27, "inner drug releasing layer, if" should be changed to --inner drug releasing layer 13, if--.

Signed and Sealed this

Nineteenth Day of August, 2008

JON W. DUDAS
*Director of the United States Patent and Trademark Office*